Figure 1:
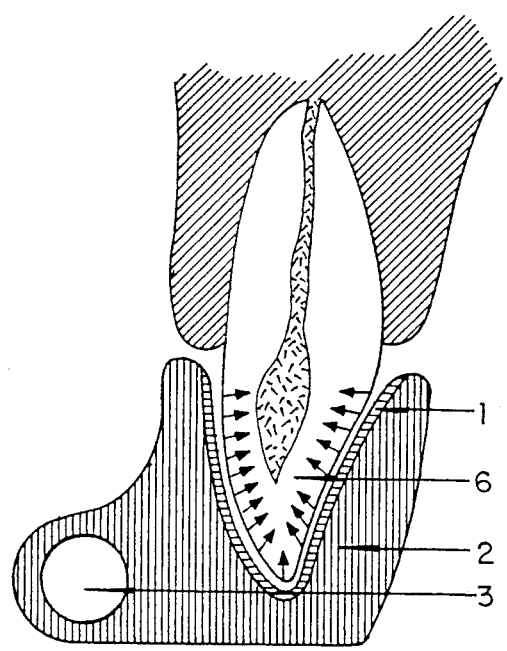

United States Patent [19]

Torres Zaragoza

[11] Patent Number: 4,983,381
[45] Date of Patent: Jan. 8, 1991

[54] METHOD AND DEVICE FOR PRODUCING THE WHITENING OF LIVE TEETH WITH PATHOLOGICAL AND NORMAL COLORATIONS

[75] Inventor: Vicente M. Torres Zaragoza, Valencia, Spain

[73] Assignee: Futura Medical S.A., Spain

[21] Appl. No.: 39,628

[22] Filed: Apr. 16, 1987

[51] Int. Cl.$^5$ ...................... A61C 5/04; A61C 13/08; A61K 7/20
[52] U.S. Cl. .......................... 424/53; 424/49; 433/39; 433/229; 433/203.1; 433/215; 433/216; 433/217.1
[58] Field of Search ................... 433/216, 217.1, 229, 433/39, 215, 203.1; 424/49, 53

[56] References Cited

U.S. PATENT DOCUMENTS

| 4,012,842 | 3/1977 | Vit | 424/53 |
| 4,661,070 | 4/1987 | Friedman | 433/229 |
| 4,718,849 | 1/1988 | von Weissenfluh et al. | 433/229 |
| 4,818,231 | 4/1989 | Steiner et al. | 433/229 |
| 4,836,782 | 6/1989 | Gonser | 433/229 |

FOREIGN PATENT DOCUMENTS

| 286766 | 10/1988 | European Pat. Off. | 433/216 |
| 2848237 | 5/1980 | Fed. Rep. of Germany | 433/217.1 |
| WO85/2112 | 5/1985 | World Int. Prop. O. | 433/217.1 |

Primary Examiner—Ronald W. Griffin
Attorney, Agent, or Firm—Ladas & Parry

[57] ABSTRACT

A method and a device are described for producing the whitening of live teeth with pathological and normal colorations, destined to whitening any tooth with normal color and furthermore eliminating the pathological coloration produced by aetiologies of different origin. The whitening of the teeth (6) is effected applying different chemical products to the dental enamel, covering the teeth to be treated with a metallic plate containing an absorbent material with a chemical whitening product which acts in the presence of heat and provokes the reaction of said product which will act on all sides of the dental drown, producing whitening of the teeth. The device is constituted, in essence, by a whitening device, comprised by a thermic heating unit, whether or not controlled by microprocessor, heating elements, temperature, time and alarm sensors and controls.

21 Claims, 7 Drawing Sheets

METHOD AND DEVICE FOR PRODUCING THE WHITENING OF LIVE TEETH WITH PATHOLOGICAL AND NORMAL COLORATIONS

The present invention refers to a new method and device for producing the whitening of live teeth with pathological and normal colorations.

For several decades different whitening products and techniques have been used to produce whitening of the teeth, not having become generalised or been commercialised owing to their unreliable results and difficult application, no equipment being available in the market for carrying out such treatment with good results and good clinical applications.

For whitening teeth with normal colorations no method whatsoever, or device, has ever been applied, the present invention being the first also applied to normal teeth providing some optimal results within a short period.

Change in teeth coloration can be due to many aetiologies or causes, including localized, generalized, environmental, hereditary ones, etc. . . . , certain antibiotics, fluorosis, etc. . . . , serve as examples.

Two types of patients could be distinguished to whom this new invention is applied. One type would be those persons who, their teeth coloring being considered normal, wish to whiten them for aesthetic improvement. Another type of persons are those having pathological colorations; in these cases there are serious psychological, social and aesthetic problems, with recourse being had to the Dentist or Stomatologist, he having neither the procedure nor means to carry out whitening, the only solution being to cover the tooth by means of caps with aesthetic fronts generally of porcelain, this procedure being highly costly.

The described process and equipment are the result of research carried out by the applicant in connection with his doctoral thesis relating to teeth whitening in the School of Stomatology Studies of the Faculty of Medicine of the University of Valencia (Spain). The initial process was patented in Spain by the applicant, being patent of invention No. 528.007, granted 3 Jun. 1985.

There have been subsequent major improvements to his doctoral thesis and to Spanish Patent No. 528.007, developed and researched at a Stomatology Research Centre, the applicant being the owner and director of the same, and also being a doctor in medicine and stomatologist.

The great advantage of the method of the present invention over what currently exists is the modus operandi and equipment used for applying the heat and the chemical whitening product to the teeth, as well as the use of different new materials as soft tissue protectors (gums and buccal mucous) during the treatment. Other advantages are the use of ultrasounds of variable force and intensity, ultraviolet rays and laser rays to facilitate penetration of the chemical whitening product into the teeth, activating, catalyzing and supplying energy for a greater whitening effect, considerably reducing the duration of treatment, obtaining better results, besides easier clinical application.

Henceforth dental professionals, stomatologists, odontologists, dentists, hospital staff, nurses, assistants etc., will have available the equipment and the procedure to enable whitening of teeth showing pathological coloration through whatever aetiology, or else of normal color with capacity for solving so broad a problem, applying it to anyone at all upon request.

Bearing the above in mind, the invention proposes a method and device for whitening live teeth with pathological and normal colorations, in such a way that by means of said method and device some optimal results are obtained in a short period of time, through a process easily applied to anyone wishing to have whiter teeth.

Accordingly, the method to whiten live teeth with pathological and normal colorations, the object of this invention, is characterised in what various chemical products are applied to the dental enamel, such as a grease-removing enamel cleanser, an acid engraving is performed and the humidity removed from the adamantine tubules. The crowns of the teeth to be treated are covered by means of a metallic plate containing an absorbent material with a chemical whitening product basically comprising 30% to 70% by weight of hydrogen peroxide, alkalines and salts, which product is a mixture of active and surfactant components in ratios defined for each case, being a reagent, reacting with the coloured compounds and determining the destruction of molecular structures which absorb characteristic bands of the visible spectrum which produced the dental color, the chemical whitening product being constituted by reagents which catalyze the reaction with the colored substrate, as well as by substances allowing greater and quicker diffusion of the reagents through the physical tooth structure achieving the enamel-dentine union, because the chemical whitening product acts in the presence of heat, which determines the reaction of said product which will act on all sides of the dental crown, producing whitening of the tooth.

In accordance with the invention, during the treatment a separator product and chemical and physical (metallic) protectors are used, as well as, following the treatment, sealants of the enamel which determine that the chemical whitening product remains insulated inside the tooth and continues acting for 24–48 hours after treatment.

The temperature relation at which the treatment is carried out is regulated automatically and the calories are controlled which it is necessary to produce at each moment so that the temperature will remain constant, preferably at an interval of 40 degrees Centigrade to 55 degrees Centigrade, said temperature being indicated periodically by digital or visual indication, the treatment time being automatically controlled and shown by digital or visual indication as well as being selected and regulated by external control.

With the aim of catalyzing the reaction of the chemical whitening product with the dental colorants, ultraviolet rays are applied. Said rays, which are administered after each application of the chemical whitening product, are low, medium and high powered laser rays, determining catalysis of the reaction of the chemical whitening product and acceleration of the whitening effect in the teeth.

In accordance with another aspect of this invention, soft tissue protectors are applied, polymerization and hardening being effected by means of an activator, as well as a metallic protector being applied to avoid diffusion of the chemical whitening product.

Finally, at the end of treatment a sealant of the enamel is applied to close the adamantine tubules, producing insulation of the chemical whitening product incorporated into the tooth, and facilitating its internal breakdown.

The device which operates in accord with the process object of the invention, which likewise constitutes an object of the latter is, in essence, comprised by a whitening device, constituted by a thermic heating unit, whether or not controlled by a microprocessor, heating elements, temperature, time and alarm sensors and controllers.

In accordance with an additional embodiment of the invention, a thermocube or thermo-containing plate is envisaged, generally of aluminum or rustfree metal, a hollow being provided in said thermocube sufficient for its proper adaptation to each particular case.

The thermocube or thermocontaining plates are made individually or in standard fashion for each maxilla, the reversible and reciprocal connection of the two thermocubes or thermocontaining plates being made simultaneously in both maxillae, or said thermocubes are otherwise doubles of a single piece.

In accordance with this invention, the heater of the thermic unit is constituted by a low frequency powered transistor acting as a thermoelectrical sensor producing and measuring the heat which is applied to the thermocube or thermocontaining plate. Said transistor or heater, which constitutes the thermic heating unit, is placed inside a capsule or circular surface placed in the thermocube or thermocontaining place, by some holding or friction mechanisms.

Furthermore, in accordance with another embodiment object of the invention, into the thermic heating units a microprocessor is incorporated with program and memory adapted for the coupling of a pulpmeter to measure the amount of tooth vitality, a colormeter for study and evolution of the color before and after treatment, an ultraviolet ray emitter, ultrasound emitter and laser ray emitter as catalysts of the chemical whitening product and, to facilitate entry thereof into the teeth, a keyboard likewise being provided which transmits the details and information which is displayed in a monitor.

The ultrasound emitter can be independent, or incorporated into the same thermic heating unit.

The metallic protector consists of a thin prefabricated metallic sheet, in its lower part holding the chemical whitening product left over from the thermocube or thermocontaining plate.

The chemical whitening product which is used in the process of the invention is a mixture of active component, in defined ratios for each patient, depending on his characteristics and aetiology and in its entirety having the following properties: it is a reagent product in the pH and temperature conditions under which the treatment is performed which, in contact with the colored compounds, by means of a chemical reaction of adding, oxidizing and reducing, destroys the molecular structures which absorbed characteristic band of the visible spectrum, which consequently produced the pathological or normal color.

In this way, even without eliminating the substrate responsible for the pathological or normal coloration, same is modified, becoming colors, thus whitening the teeth.

Along with the active product mentioned above, the chemical whitening product is also formed by reagents which catalyze the reaction with the colored substrate, as well as by substances allowing greater or quicker diffusion of the reagents through the physical structure of the tooth, achieving the enamel-dentine union.

The chemical whitening product can have incorporated an anaesthetic to eliminate or reduce tooth sensitivity during treatment, making application trouble free.

The thermocubes or metallic thermocontaining plates, preferably of aluminum, stainless steel or other metal not readily oxidizable by the hydrogen peroxide, are prepared for each person as usual procedure in the dental prosthesis laboratory: polishing, grinding, glossing, etc., needing a correct design and sufficient thickness for properly and evenly transmitting the heat. These thermocubes should cover the whole clinical crown of the teeth to be treated, from the gingival edge to the incisor edge, whether buccal or vestibular, palatine or lingual.

Were the metal other than aluminum or stainless steel, it should be given an outer coating with an antioxidizing material as protection against the chemical whitening product.

Subsequently, in the zone to contact with the teeth, if possible with a thermic conductor adhesive, an absorbent material is adhered which will, during the treatment, be saturated with whitening agent so that this is in contact with the teeth. This absorbent material will have to be basically 100% cotton or other material not deteriorating on coming into contact with hydrogen peroxides.

Another way to make the thermocontaining plates or thermocubes will be industrially, that is, by microfusion and injection with prefabricated molds resulting in an extensive and diverse set of standard thermocubes or thermo-containing plates for selection, adaptation and preparation depending on each patient's needs, subsequently checking their correct adaptation whether in the upper or lower maxilla, this set of standard thermocubes being of use in 100% of cases.

To select the standard thermocubes one starts from some plaster casts of the upper and lower maxilla.

Afterwards the plaster model is cut out until the distal side of the last tooth to treat: whitening of canine to canine (six teeth) is advised, or of the first premolar to first premolar (eight teeth).

Thereafter the curvature of the incisor edges of the teeth of the model is transferred to the vertibular or buccal curvature of the thermocubes, making the center line coincide (mesial sides of the central incisors) with the center line of the thermocube.

When the curvature of the incisor edges of the teeth is made to coincide with the vertibular or buccal curvature of the selected thermocube, this will be the right one for carrying out the treatment.

Hence two thermocubes will be selected in each person, one for the upper teeth and the other for the lower teeth.

The connecting part of the thermocubes to one another is reversible, that is, the same set of thermocubes serves for the upper and lower maxilla indistinctly, transmitting the heat from the connection with the heater to both thermocubes as between one another, the two thermocubes and heater forming an entire unified block.

For adapting the length of the standard thermocube, the center line of the teeth in the plaster mold or in the mouth is made to coincide with the center of the selected thermocube; a line is to be marked in this thermocube which will coincide with the distal side of the last tooth to be treated on both sides.

The thermocube will be cut lengthwise along that line corresponding to the distal side of the last tooth to be treated. Hence, this way the length of the standard thermocube will be determined.

For adapting the height of the standard thermocube the height will be measured of the teeth to be treated on the plaster model or in the mouth. This height is transferred to the standard thermocube from the incisor bottom of same until the height selected in the teeth, increasing this in accordance with the thickness of the absorbent material to be placed subsequently.

The thermocube is to be cut to the selected height.

Adaptation of the height tooth by tooth can be done cutting out in the thermocube the difference in height that exits between the teeth.

For placement of the absorbent material with a small spatula or like instrument, in the zone where the teeth of the thermocube are to be located, a very fine layer of thermic conductor adhesive is applied, and afterwards the absorbent material is pressed, adapted and adhered thereto.

Once adhered the leftover absorbent material is cut out in the height and length of the standard thermocube.

If it is wished to perform the treatment in a single maxilla, the neutral opposing plate is to be placed, counteracting the thermocube, so that the heater of the thermic unit can be placed in position.

With standard thermocubes their individual manufacture is avoided, the same results being obtained at much lower cost.

There are various kinds of thermocubes or thermocontaining plates which would vary in their design, depending on their connection and adaptation to the apparatus system of apparatus, used as heating unit, ultrawave apparatus, laser and ultraviolet ray apparatus, etc.

With this kind of standard thermocube the treatment can be performed simultaneously in both maxillae, considerably reducing treatment time.

The thermocubes are subsequently tested in the patient's mouth, to see if they adapt properly to the teeth.

The functions of the thermocubes are:

1-To have great humectant and absorption power of the whitening agent by means of the absorbent material;
2-Great adaptability of the absorbent material to the thermocube and to the teeth;
3-Adhesive of the thermic non-insulating absorbent material;
4-Uniform transmission of the heat throughout the whole;
5-Location of the temperature sensor close to the teeth, measuring a real temperature;
6-Reversible connection of the thermocubes and adapted to the heater of the thermic unit such that the treatment can be carried out simultaneously in both maxillae in considerably shorter treatment time;
7-Low financial cost on manufacture being standard and with mass production;
8-Transmitting the ultrasounds to the whitening agent and to the teeth;
9-Non-retention of dirt or organic matter since they are polished.

The different heating equipment and accessories used in the present invention will be described below. One of these heating units operates either by means of a transistor-sensor which works time-sharingly as heater and temperature sensor or by means of a heater resistance with a temperature sensor incorporated or independent therefrom.

The heat can also be supplied by means of a heat fluid circuit with its corresponding sensor.

As an important condition all of the heating units conform to the international safety norms for electro-medicinal and dental equipment.

Another of the thermometrical heating units is based on its action being exercised in the heat given off by ultrasounds that is, we take advantage of this to facilitate entry of the chemical whitening product, as well as to catalzse the reaction of the same, having in turn a sensor which will measure the treatment temperature as exactly as possible.

The heating units can have a display for digital reading of the treatment temperature, as well as digital reading of the treatment time with an alarm activated every three or every five minutes, to signal and carry out fresh incorporation of the chemical whitening product.

Help is in turn given to catalzse the reaction of chemical whitening product by means of ultraviolet light and laser rays. The heating units can be operated electronically by means of a microprocesor with program and memory, also able to possess a pulpmeter to measure tooth vitality, a colormeter for study and evolution of the color before and after treatment, ultraviolet ray emitter, ultraware emitter and laser ray emitter as catalysts of the chemical whitening product and facilitating entry of same into the teeth.

Low, medium and high powered laser rays can likewise be applied independently to whiten the teeth without the chemical whitening product, this laser radiation emitting a particular wave length depending on the type and intensity of the coloration.

These apparatus can in turn, by means of a microprocessor, effect comparative studied before and after the treatment, as well as obtaining variations and means secured in various treatment sesions. All of the data and information can be transmitted by means of a keyboard appearing in a monitor, easily read and understood.

Once the treatment time is selected, treatment itself then begins, capable of being interrupted at any time to resume whenever wished, the real treatment time being calculated, if desired.

EXAMPLES

Example 1

In the first place, we will carry out a diagnostic study of the case, with a differential diagnostic between pathological coloration with its aetiology which has produced it and normal colorations by simple visual observation or a colormeter, taking into account the colors shades and their intensity.

Next we will perform a study of the quality of the dental enamel, whether it is normal or shows alterations such as hypoplasia, cracks, fissures, etc.

The selection criteria for the case having been studied, we will carry out an in-depth prophylaxis of the entire mouth and will record the color of the teeth by means of a colormeter and photographs and, according to the shade and color intensity, we will have a guide to the number of sessions.

Thereafter we will obtain some models of the patient's teeth, of the upper and lower maxillae in plaster making some impressions taken with reversible or irreversible hydrocoloids.

These models will serve to prepare, chose or select some metallic plates which cover the crowns of the teeth on all four sides, mesial, distal, buccal or vestibular, palatine or lingual, throughout the present Specification referred to as thermocubes or thermocontaining plates which can, in turn, be made individually for each person, or chosen from a standard set in various shapes and sizes, selecting the most accurate ones for each person or patient.

These thermocubes or thermocontaining plates can in turn have designs and shapes, capable of being applied for a single maxilla or for both maxillae simultaneously. Through these thermocubes or thermocontaining plates the transmission of heat will take place from the thermometrical or ultrawave heating unit to the chemical whitening product for catalyzing its effect and to the teeth themselves.

The patient can be given an ultrasound cleaning and then subsequent polishing of the teeth by means of bicarbonated salts and water under pressure whereby the dental bacterial plaque is eliminated and the tooth enamel cleaned to facilitate its later preparation.

Subsequent application of trunk anaesthetic for the teeth to be treated is optional. The patient rinses his mouth and the teeth are air-dried. A lip separator is applied during the entire treatment session to clear the field or zone to be treated.

On the dental enamel a chemical product is applied producing cleansing and more thorough degreasing thereof which, along with a subsequent acid engraving (for example, orthophosphoric acid at 36%–50%) in the enamel, is of vital importance for leaving the entry to the enamel tubules free where the whitening agent penetrates.

This grease-remover and cleanser is applied for 5 to 10 minutes and the acid for 2 minutes.

Thereafter irrigation with water takes place and the teeth are washed, afterwards air-dried.

So far these products have been applied in both maxillae.

Next the upper maxilla is prepared, with a cotton wad and tweezer applying a very volatile product which extracts the humidity and the water from the enamel tubules, these being left free of liquid so that the whitening agent can penetrate quicker without becoming diluted. Afterwards the teeth are air-dried.

Subsequently, the gum is air-dried and, with a small brush, a chemical separator product is applied on the adherred gum from the gingival edge until the mobile gum (near the bottom of the vestibule), both in buccal or vestibule and in palatine. This product will avoid direct contact of the soft tissue protector with the mucous or gum and once polymerized, and this protector being removed, no tearing or surface peeling of the gum or mucous will occur. If this separator is not applied on the gum or mucous, on removing the protector this tearing or surface peeling of the gum or mucous would cause the patient discomfort during the repair and healing period.

Afterwards the soft tissue protector is applied on the separator product by means of a small spoon, small spatula, ball instrument, etc. . . . , metallic or plastic. The buccal or vestibule adhered gum is covered from top to bottom, that is, from the bottom of the vestibule toward the gingival edge, likewise covering the gingival festoon and the interdental papillae. This soft tissue protector is a cyanoacrylate of a certain viscosity so that it can be better applied.

Thereafter the soft tissue protector is activated by means of its activator, rapidly hardening "in situ".

The buccal or vestibule zone having concluded, it will likewise be applied in the palatine zone.

Afterwards a second coating of soft tissue protector is applied and activated on top of the first one. The application of the soft tissue protector has to be twofold in two superimposed layers.

The area to apply the soft tissue protector has to be slightly greater than that corresponding to the teeth to be treated.

This soft tissue protector is very important since, without it, the treatment would be very painful and more or less deep lesions would be produced in the gums or mucous, caused by the chemical whitening product. With the application of the soft tissue protector entire impermeability of the gums and mucous is achieved with respect to the whitening agent, the latter not producing any lesion whatsoever or discomfort for the patient. Moreover, this soft tissue protector is transparent, which is a great advantage since, if due to a defect in the clinical application there were to be a filtration pore through the protector, owing to its transparency, a small initial whitener lesion could be produced and more protector could be applied on top of such filtration pore.

To date there had been no type of effective protection against these oxidising whitening agents, the present method, and device underlying this invention, achieving this.

Thereafter the lower maxilla is prepared, the same operation being performed as in the upper maxilla.

In this lower maxilla a metallic protector is placed, first adapted to the model and placed after and over the first soft tissue protector; the metallic protector is adjusted and adheres properly, thereafter putting down the second layer of the protector covering the metallic protector just a little so that there will be no filtrations, afterwards activating said protector.

The metallic protector having been put in place, the buccal or vestibular wings are folded over in their back part toward the tooth and a long cotton wad is so placed that the leftover whitening agent will not flow backwards, and can run out of the thermocube. The whitening agent which is deposited in the lingual zone of the metallic protector should be adsorbed by suction by the dental equipment.

The metallic protector (of aluminum or other rust-free metals) is very important, since it avoids diffusion of the chemical whitening product in the bottom of the mouth and bottom of the vestibule, and consists of a slim pre-shaped metallic sheet, as per the design in the corresponding figure, which adapts very well. Its configuration and manufacture is standard and in various sizes, for adapting to the different size of the patients' lower maxillae.

Once the dental enamel has been prepared and the soft tissues protected in the entire zone to be treated in both maxillae, the prepared whitening agent is applied, which can in turn have incorporated an anaesthetic to avoid possible sensitivity and irritation of the dental nerve endings, avoiding or much reducing discomfort to the patient during the treatment session.

This agent or chemical whitening product is incorporated into the absorbent material of the upper and lower thermocube depositing various drops until said absorbent material is saturated and wet.

From this clinical step on it is advisable to use surgical gloves to avoid contact by the dental professional with the whitening agent.

Both thermocubes are connected to one another and to the heater and temperature sensor of the thermic unit which will be put into operation.

The thermocubes are correctly placed in the teeth, covering them entirely but without bringing excessive pressure to bear. The patient should close his mouth in a protrusive way since the thermocubes are manufactured in that position.

The leftover whitening agent on closing the mouth and exercising pressure will be deposited in the metallic protector of the lower maxilla, being absorbable by cotton wadding or suction by the dental unit.

Every three to six minutes some more drops of the agent or chemical whitening product will be applied to the thermocube; the thermic unit can mark this time interval by acoustic signals.

The treatment temperature can range from 40 degrees C. to 55 degrees C. approximately, depending on colorations and patients.

The real duration of each treatment session in the two maxillae simultaneously is one hour, a minimum of thirty minutes being considered sufficient.

The application time in both maxillae having elapsed, the soft tissue protector is removed with a small spoon or pail making slight movements in the handle and at the same time with water wetting the zone that is going to be prised loose.

Example 2

In patients with dental class III, where the upper and lower thermocube cannot be applied simultaneously, the treatment of one maxilla is carried out in each session, adapting the neutral plate to the thermocube for connection thereof to the thermic unit. The treatment of one maxilla per session is applicable to all those patients who might wish it.

The treatment session having concluded we will record the new color obtained, making a comparative study to allow assessment of the results.

Thereafter, if of interest, the dental enamel can be sealed so that the whitening agent introduced into the tooth continues to act, avoiding contact with the buccal area, saliva, diet, etc. . .

The result which is obtained by means of the method and device object of the invention is a whitening in the entire clinical crown of the teeth to be treated, that is, all four sides of the teeth, acting against all of the existing colorants in the dentine and dental enamel. Treatment time is reduced to the utmost, as well as the number of sessions.

The whitening achieved is uniform in all of the teeth treated, reducing the difficulty of application, being a simple and effective treatment.

The temperature applied to the teeth is controlled in an exact and reliable way, providing us with a great work guarantee. The soft tissues are entirely protected, susceptible to contact with the whitening agent. Similarly, application of the chemical whitening product is facilitated in all of the teeth to be treated, much improving the results.

Figure 2:
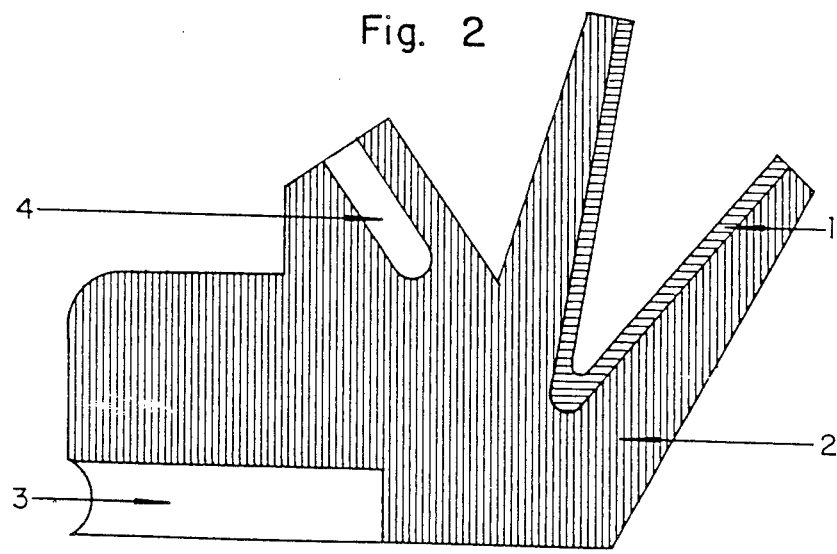
Figure 3:
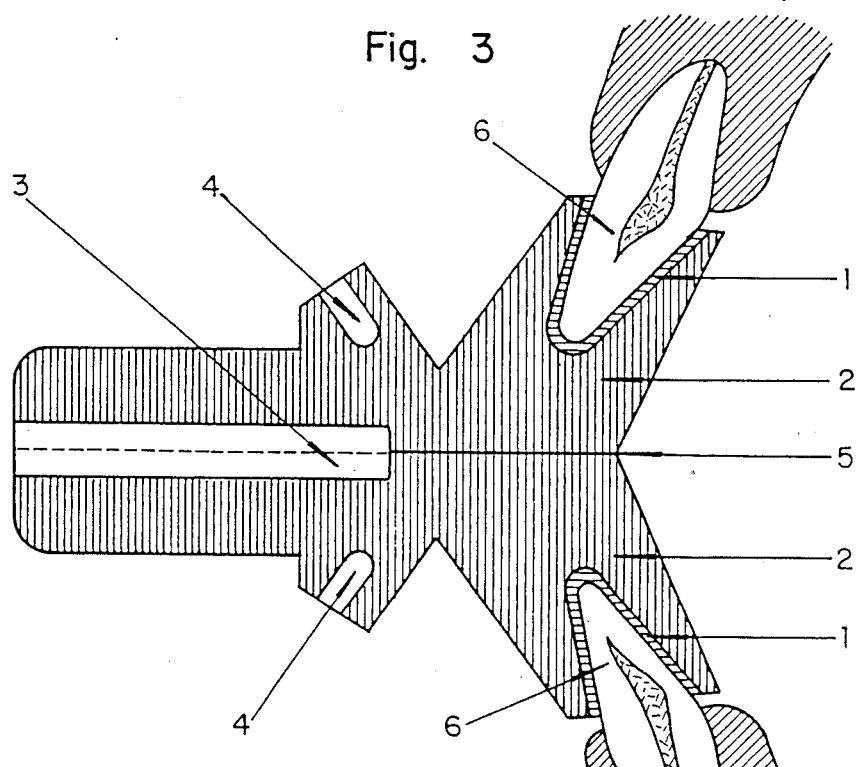
Figure 4:
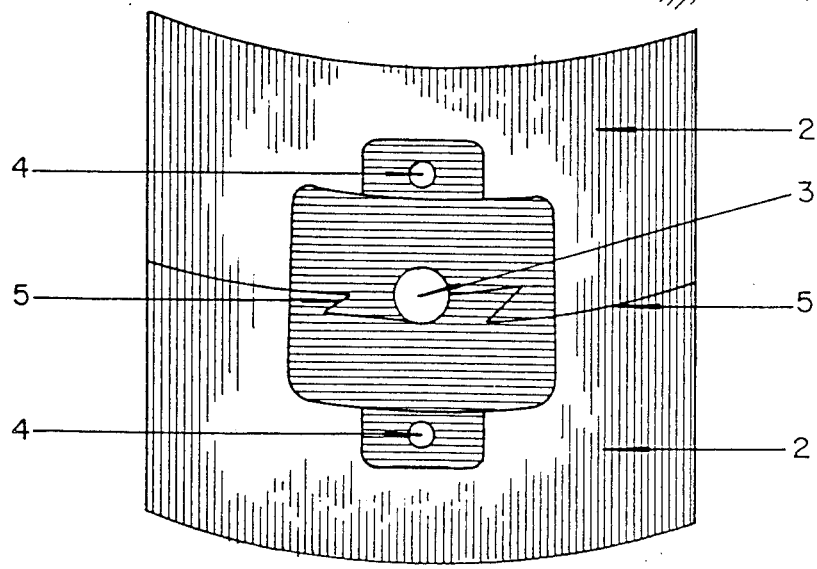

Supplementary to the operative stages set forth above, which constitute the method and device of the invention, a detailed description will be provided of the device used, for which purpose a set of drawings is attached to the present Specification wherein, merely as a guide, and not restrictively, the following is represented:

FIG. 1, shows a side view of the thermocube or thermocontaining plate 2 made individually, with placement of the absorbent material 1 of the chemical whitening product or whitening agent and the connecting space 3 of the thermic heating unit, applied to the teeth 6;

FIG. 2 shows a side view of the standard thermocube or thermocontaining plate 2 with the placement of the absorbent material 1 of the chemical whitening product or whitening agent and the connecting space 3 of the thermic heating unit and connecting space 4 for placing and locating the temperature sensor;

FIG. 3 shows a side view of the thermocubes or thermocontaining plates 2 upper and lower, connected to one another 5, with the connector space 4 for placing and locating the temperature sensor, with the absorbent material 1 of the whitening agent or chemical whitening product and applied simultaneously to the teeth 6;

FIG. 4 shows a front view of two thermocubes or thermocontaining plates 2 upper and lower, connected to one another 5, with the connector space 3 for the heating unit, with the connector space 4 for placing and locating the temperature sensor.

Figure 5:
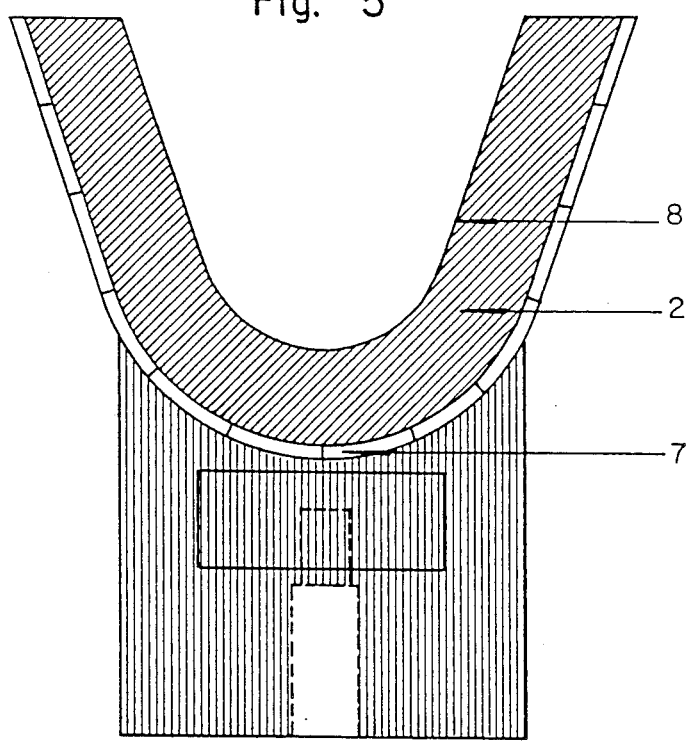
Figure 6:
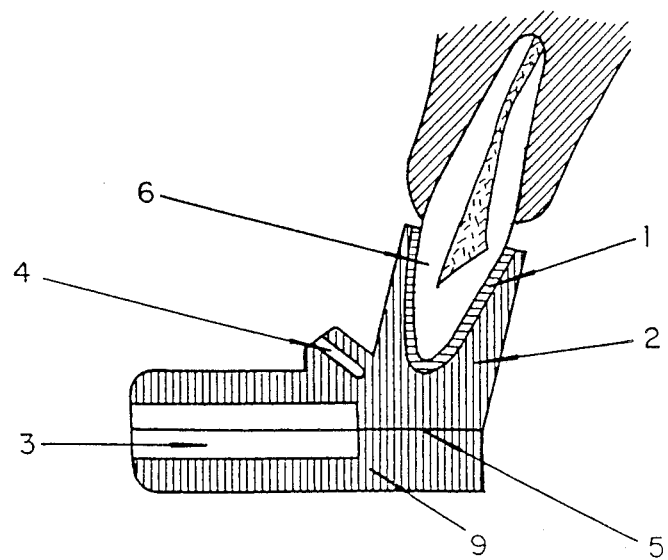
Figure 7:
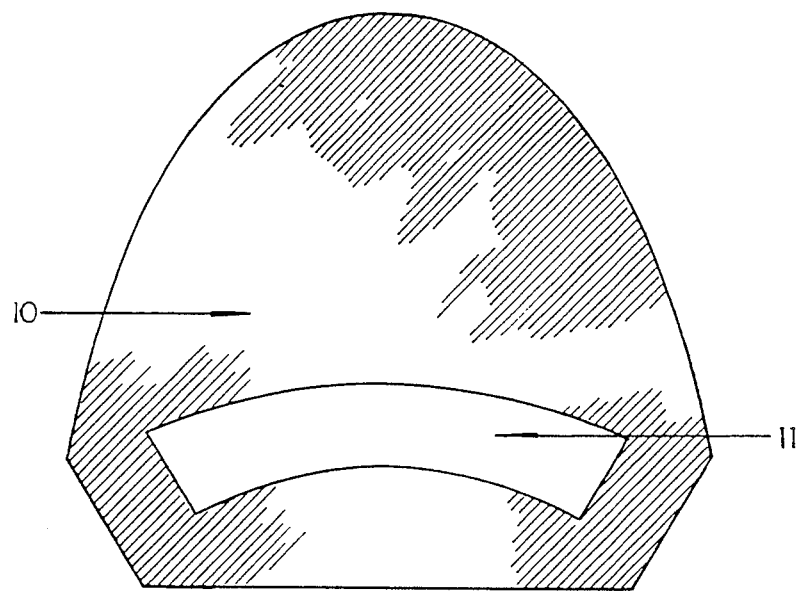
Figure 8:
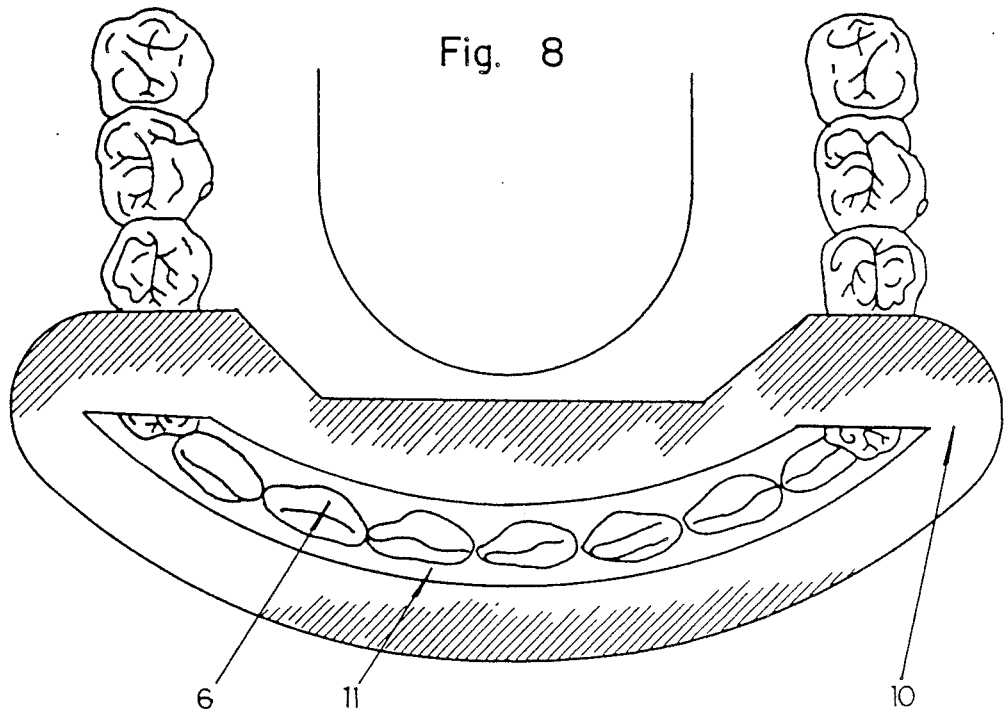
Figure 9:
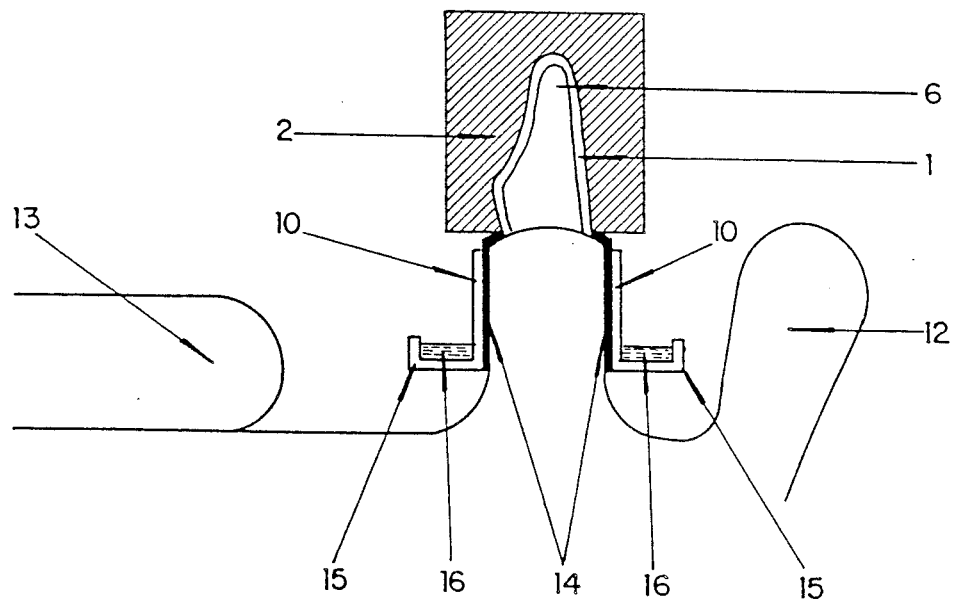
Figure 10:
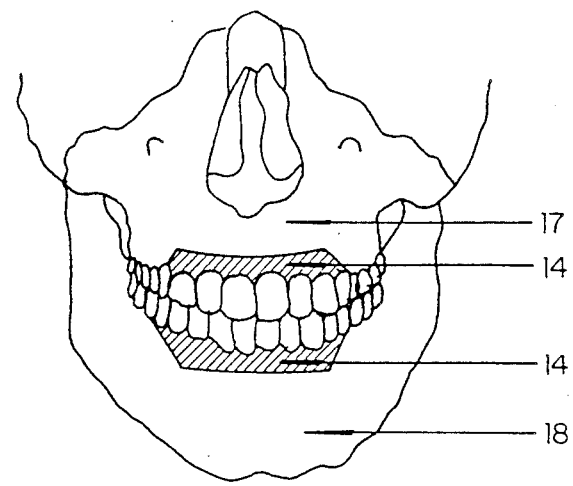
Figure 11:
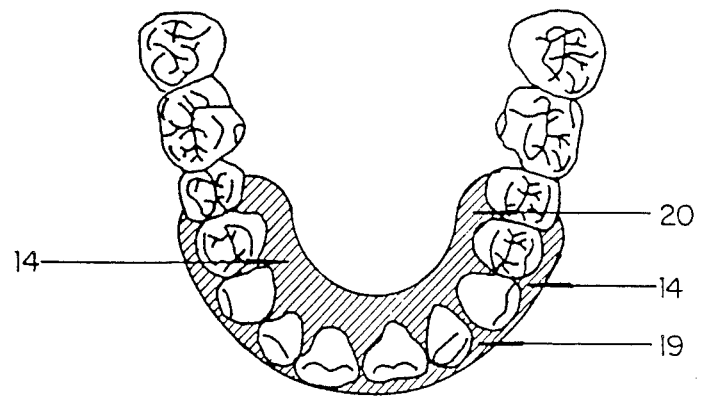
Figure 12:
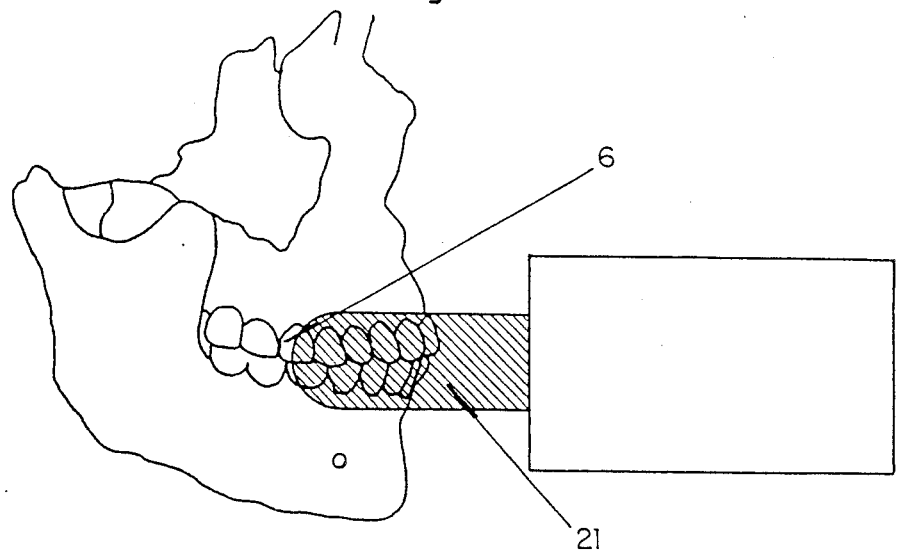
Figure 13:
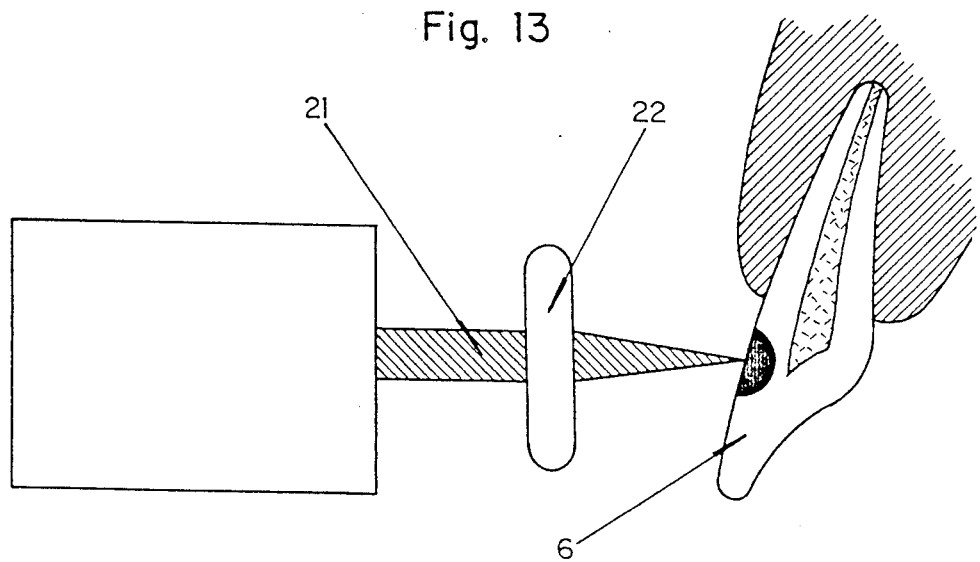

FIG. 5 shows a plane view of a standard thermocube or thermocontaining plate 2 with its vestibule or bucal curvature 7 and palatine or lingual 8, curvatures which vary within the set of standard thermocubes or thermocontaining plates for selection and adaptation of the same;

FIG. 6 shows a side view of a standard thermocube or thermocontaining plate 2 connected 5 to the counteracting neutral plate 9 for the treatment of one maxilla with the connector space 3 of the heating unit and connector space 4 for the placement and location of the temperature sensor, with the absorbent material 1 of the chemical whitening product or whitening agent and applied on the teeth 6;

FIG. 7 shows a plane view of the metallic protector 10 for the upper maxillar with a slot or central aperture 11 to locate the teeth and reach the soft tissues;

FIG. 8 shows a plane view of the location of the metallic protector 10 in the lower maxilla with the slot or central aperture 11 to be able to go past the teeth 6. This is a plane view where we see the zone to be protected from the dropping of the chemical whitening product or whitening agent whether in the vestibule or bucal zone or lingual one and bottom of the mouth;

FIG. 9 shows a side view of the lower maxilla. In the front zone the lip 12 is found and in the back zone the tongue 13; we see the thermocube or thermocontaining plate 2 adapted to the teeth 6 with its absorbent material 1 saturated with whitening agent or chemical whitening product, the location being seen of the chemical soft tissue protector 14 and the adaptation and fit of the metallic protector 10, with a retaining shape or cavity 15 for collecting the whitening agent or chemical whitening product 16 proceeding from the thermocube, whether in the vestibule surface or buccal or lingual one;

FIG. 10 shows a front view of the application of the chemical soft tissue protector 14 in the upper maxilla 17 and lower maxilla 18;

FIG. 11 shows a lower or upper view of a maxilla with the chemical soft tissue protector 14 applied in the vestibule or buccal zone 19 and in the palatine or lingual zone 20;

FIG. 12 shows a side view of the application to the teeth 6 of ultraviolet or laser rays 21 of low, medium and high power; and FIG. 13 shows a side view of the application to the teeth 6 of ultraviolet or laser rays 21 of low, medium and high power, pointed in shape by means of a lens 22.

I claim:

1. A method for whitening a live tooth or for simultaneously whitening a plurality of live teeth, said tooth or teeth containing colorants which impart to the tooth or teeth a color or colors, said tooth or teeth having enamel and enamel tubules, said tubules containing water or water vapor, said method comprising acid engraving the enamel to open the enamel tubules and extracting the water or water vapor from the tubules, covering the tooth or teeth with a metallic plate having an absorbent material containing a chemical whitening agent so that the tooth or teeth is covered by the plate with the absorbent material in contact with the tooth or teeth, said whitening agent being effective to react with and destroy the colorants when activated, heating the plate to cause the whitening agent to be heated to a temperature sufficient to activate it, and causing said absorbent material to be pressed against the tooth or teeth so as to cause the activated whitening agent to be released into the tubules and to diffuse through the tubules to the enamel-dentine junction of the tooth or teeth whereby to react with and destroy the colorants and thereby to whiten the tooth or teeth.

2. A method as claimed in claim 1 further comprising applying a cleanser or cleansers to the teeth prior to the acid engraving to clean or degrease the enamel or both.

3. A method as claimed in claim 2 wherein the whitening agent comprises $H_2O_2$ and is present in an amount of from about 30–70%.

4. A method as claimed in claim 3 wherein the whitening agent further comprises a reagent, which catalyzes the reaction between the whitening agent and the colorants, and a substance or substances which help to diffuse the whitening agent through the tooth or teeth.

5. A method as claimed in claim 3 further comprising protecting the gums of a patient to be treated with the method by covering at least part of the gums with a chemical compound which is resistant to the whitening agent or separating the gums from the whitening agent with a metallic barrier or both.

6. A method as claimed in claim 5 wherein the gums are protected with a chemical compound which comprises a cyanoacrylate.

7. A method as claimed in claim 6 wherein the absorbent material has been saturated with an initial amount of the whitening agent prior to covering the tooth or teeth with the plate and wherein the method further comprises applying an additional amount of the whitening agent to the absorbent material after the initial amount of whitening agent has been released into the tubules and then causing said additional amount to be released into the tubules.

8. A method as claimed in claim 7 further comprising sealing the enamel after the whitening agent has been released into the tubules in a desired amount.

9. A method as claimed in claim 1 further comprising regulating the heating of the plate by means of a thermostat to keep the temperature of the plate constant at a temperature of between about 40°–55° C.

10. A method as claimed in claim 8 wherein the whitening agent is caused to be released into the tubules for a desired period of time, the method further comprising monitoring the time and the temperature of the plate by means of a visual or digital indicator.

11. A method as claimed in claim 1 further comprising subjecting the whitening agent to laser rays to catalyze the reaction between the whitening agent and the colorants.

12. An article for use in whitening teeth comprising first means for covering substantially the entire crown of each of a plurality of teeth, said first means comprising second means for containing a chemical agent for whitening the teeth and for releasing the chemical agent when the second means is pressed against the teeth, said first means being adapted for covering the teeth with the second means pressed against the teeth, said article further comprising third means for heating the first and second means whereby to heat the chemical agent to a desired temperature.

13. An article as claimed in claim 12 wherein said second means comprises a material suitable for absorbing the whitening agent and for releasing said agent when the material is pressed against the teeth.

14. An article as claimed in claim 13 wherein the first means comprises a thermocube or thermo-containing plate made at least in part of a rust-free metal.

15. An article as claimed in claim 14 wherein the third means comprises a heating unit which includes a low-frequency power transistor which acts as a thermo-electrical sensor to produce and measure the heat which is applied to the thermocube or thermo-containing plate.

16. An article as claimed in claim 15 wherein the heating unit is included in the third means.

17. An article as claimed in claim 16 wherein the third means further comprises means to monitor the use of the article to treat a patient.

18. An article as claimed in claim 17 wherein the means to monitor includes a microprocessor with a program and memory coupled to means for measuring tooth vitality and tooth color.

19. An article as claimed in claim 18 wherein the article further comprises an ultraviolet ray emitter, an ultrasound emitter and a laser ray emitter coupled to said third means.

20. An article as claimed in claim 14 wherein the first means comprises metallic sheet means positioned to block the chemical agent from contacting the gums of a patient to be treated when the first means is covering the teeth.

21. An article as claimed in claim 12 wherein the first means is adapted for covering a plurality of teeth in one or both maxillae of a person to be treated.

* * * * *